US006273404B1

United States Patent
Holman et al.

(10) Patent No.: US 6,273,404 B1
(45) Date of Patent: *Aug. 14, 2001

(54) METHOD OF MAKING MONOLITHIC HUB AND STRAIN RELIEF

(75) Inventors: Thomas J. Holman; John E. Arnold, Jr., both of Minneapolis; Gregory K. Olson, St. Louis Park; Todd A. Berg, Lino Lakes, all of MN (US)

(73) Assignee: Scimed Life Systems, Inc., Maple Grove, MN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/971,456

(22) Filed: Nov. 17, 1997

Related U.S. Application Data

(63) Continuation of application No. 08/461,867, filed on Jun. 5, 1995, now abandoned.
(51) Int. Cl.[7] .............................. B29C 45/14; B29C 70/72
(52) U.S. Cl. ......................... 265/276; 264/259; 604/525
(58) Field of Search .................................. 604/523–525, 604/533, 284, 905, 164, 165, 177, 178, 264; 285/114–116; 264/261, 262, 263, 267, 275, 259

(56) References Cited

U.S. PATENT DOCUMENTS

| Re. 25,788 | 6/1965 | Sheridan . | |
|---|---|---|---|
| 2,185,741 | * 1/1940 | Sorg et al. | 285/115 |
| 3,318,335 | * 5/1967 | Heller | 285/114 |
| 3,348,544 | 10/1967 | Braun . | |
| 3,720,210 | 3/1973 | Diettrich . | |
| 3,914,002 | 10/1975 | Berliner et al. . | |

(List continued on next page.)

OTHER PUBLICATIONS

Brochure, SciMed Life Systems, Inc., 1990, 1 page.

Brochure, *Technical Notes,* published on date even with or prior to Jun. 5, 1995, 2 pages.

*Primary Examiner*—Angela Ortiz
(74) *Attorney, Agent, or Firm*—Crompton, Seager & Tufte LLC

(57) ABSTRACT

A hub assembly for a catheter tube having a lumen therethrough. The hub assembly includes a hub portion having a proximal end and a distal end, and an integral connector disposed at the proximal end. A lumen is defined through the hub portion extending from the proximal end to the distal end. The strain relief includes a proximal end and a distal end is disposed at the distal end of the hub portion. The proximal end of the strain relief can be integrally connected to the distal end of the hub portion. The strain relief is preferably more flexible than the hub portion. The strain relief defines a passage configured to receive the catheter such that a lumen through the hub portion is in fluid communication with the catheter tube lumen.

24 Claims, 5 Drawing Sheets

U.S. PATENT DOCUMENTS

| | | | |
|---|---|---|---|
| 3,950,052 | * 4/1976 | Walter et al. | 339/101 |
| 4,154,244 | 5/1979 | Becker et al. . | |
| 4,198,983 | 4/1980 | Becker et al. . | |
| 4,354,495 | 10/1982 | Bodicky . | |
| 4,489,961 | * 12/1984 | Laidig | 285/116 |
| 4,509,877 | * 4/1985 | Sobin et al. | 285/114 |
| 4,511,163 | 4/1985 | Harris et al. . | |
| 4,602,808 | * 7/1986 | Herron et al. | 285/115 |
| 4,863,441 | 9/1989 | Lindsay et al. | 604/280 |
| 4,874,373 | 10/1989 | Luther et al. | 604/164 |
| 4,960,412 | * 10/1990 | Fink | 604/167 |
| 5,041,095 | * 8/1991 | Littrell | 604/167 |
| 5,085,645 | * 2/1992 | Purdy et al. | 604/167 |
| 5,125,903 | * 6/1992 | McLaughlin et al. | 604/167 |
| 5,143,409 | * 9/1992 | Lalikos | 285/116 |
| 5,167,647 | * 12/1992 | Wijkamp et al. | 604/281 |
| 5,181,750 | * 1/1993 | Reum | 285/115 |
| 5,226,898 | 7/1993 | Gross | 604/243 |
| 5,248,305 | 9/1993 | Zdrahala | 604/280 |
| 5,330,449 | 7/1994 | Prichard et al. | 604/282 |
| 5,358,493 | * 10/1994 | Schweich, Jr. et al. | 604/264 |
| 5,376,077 | * 12/1994 | Gomringer | 604/167 |
| 5,380,301 | * 1/1995 | Prichard et al. | 604/281 |
| 5,395,332 | 3/1995 | Ressemann et al. | 604/96 |
| 5,403,292 | * 4/1995 | Ju | 604/282 |
| 5,466,230 | * 11/1995 | Davail | 604/256 |
| 5,507,728 | * 4/1996 | Erskine | 604/164 |
| 5,545,151 | * 8/1996 | O'Connor et al. | 604/282 |
| 5,558,635 | * 9/1996 | Cannon | 604/164 |
| 5,558,652 | * 9/1996 | Henke | 604/280 |
| 5,695,467 | * 12/1997 | Miyata et al. | 604/280 |
| 5,803,510 | * 9/1998 | Dorsey, III | 604/264 |
| 5,830,401 | * 11/1998 | Prichard et al. | 264/262 |
| 6,113,576 | 9/2000 | Dance et al. | 604/164 |

* cited by examiner

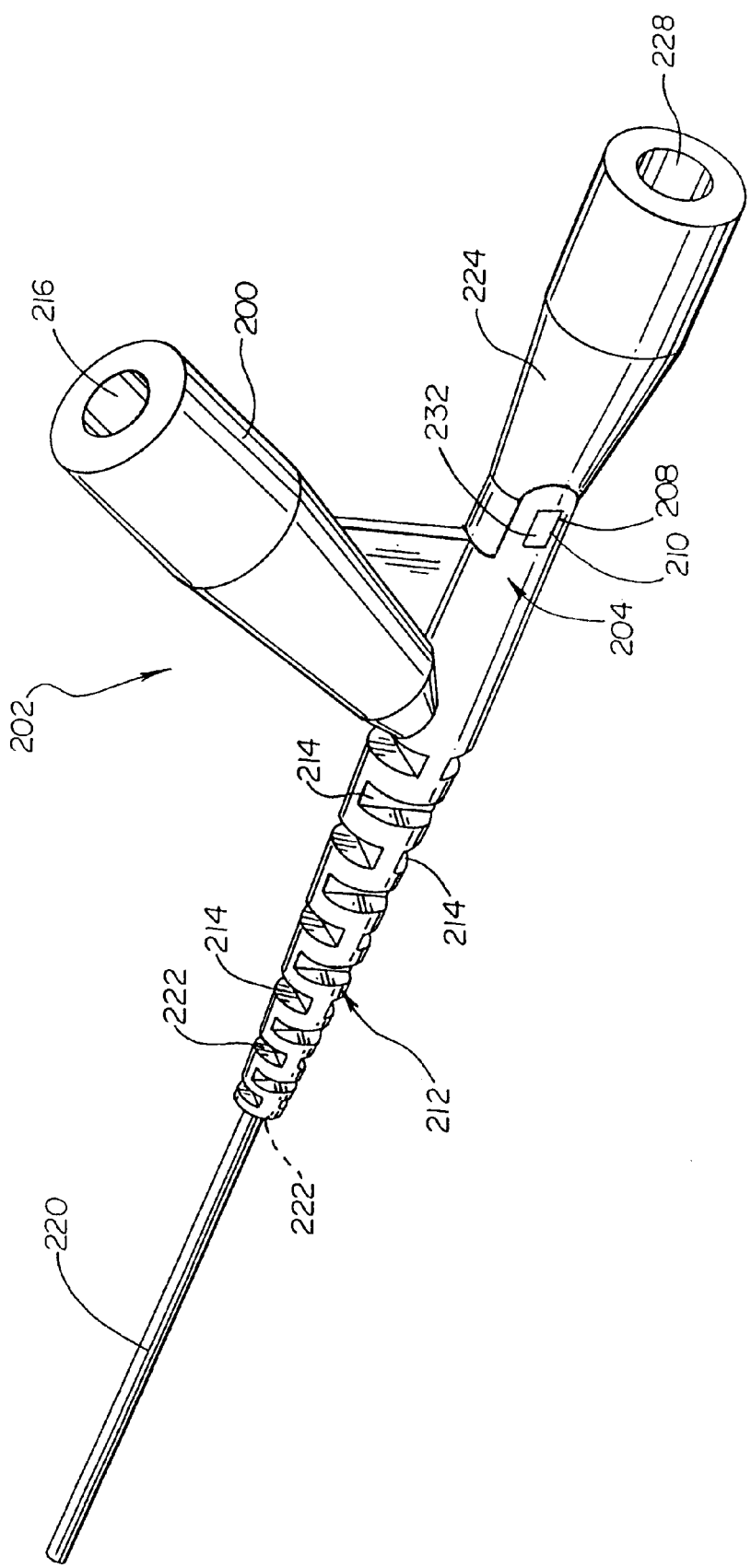

METHOD OF MAKING MONOLITHIC HUB AND STRAIN RELIEF

This application is a continuation of application Ser. No. 08/461,867, filed Jun. 5, 1995 now abandoned.

BACKGROUND OF THE INVENTION

The present invention pertains generally to the field of catheters and, more particularly, to hub or manifold assemblies connected to the proximal end thereof.

Catheters, such as guide catheters, diagnostic catheters and therapeutic catheters, for example, angioplasty and atherectomy catheters generally comprise a flexible tube having a permanently connected hub assembly at one end of the tube. The hub assembly often includes a hub and a strain relief. The hub generally includes a connector for connecting the catheter to a Y-adaptor, inflation device or the like. The strain relief generally extends from the hub along a portion of the catheter tube to provide a transition in flexibility between the hub and the tube.

Prior hub assemblies utilized a two piece construction, for example, the hub was attached to an end of the catheter tube and then the strain relief was attached in a secondary process. The primary reason for the two piece design was the different functions of the hub and strain relief required different materials or material properties. The hub is required to be harder material to withstand forces applied to the connector. The strain relief, however, must provide a stiffness transition from the hub to the catheter shaft. The strain relief material is typically soft and flexible to provide kink-resistance and added support to the catheter shaft proximate the hub.

One such hub assembly is disclosed by Wijkamp et al. in U.S. Pat. No. 5,167,647. In one embodiment, a tubular strain relief is injection molded around one end of the catheter. After the strain relief has hardened, a hub is secured to the strain relief. Alternately, an end of the catheter may be inserted into a hub. The hub and catheter can then be placed into a mold to form the strain relief around the end of the catheter and between the catheter and the hub. Wijkamp et al. also discloses simultaneously molding both the hub and the strain relief from two different materials.

Prichard et al., in U.S. Pat. No. 5,380,301, also disclose a prior hub assembly. Prichard et al. disclose a hub formed of a material having a relatively high durometer hardness in comparison to the catheter. The strain relief is preferably formed of a material having a flexibility and durometer hardness which is greater than that of the catheter, but less than that of the hub. The hub is first separately molded, then an end of the catheter is inserted into the hub. Then both the hub and the portion of the catheter proximal the hub are placed in a mold. As disclosed by Wijkamp et al., the strain relief is then molded around the catheter and between a portion of the hub and the catheter. The hub also includes openings into which molten strain relief material flows to form a mechanical bond between the strain relief and the hub.

SUMMARY OF THE INVENTION

The present invention pertains to a hub assembly including an integrally formed hub and strain relief. The hub assembly can be insert molded in a single mold using one injection process and a single material. The material can be sufficiently hard for use in forming the hub. The desired relatively greater flexibility of the strain relief is achieved by modifying the geometry of the strain relief.

In a preferred embodiment, the hub assembly in accordance with the present invention is for a catheter having a lumen therethrough. The hub assembly includes a hub portion having a proximal end and a distal end. An integral connection is disposed at the proximal end. A lumen defined through the hub portion extends from the proximal end to the distal end.

A strain relief having a proximal end and a distal end is disposed at the distal end of the hub portion. The proximal end of the strain relief is integrally connected to the distal end of the hub portion. The strain relief defines a passage configured to receive the catheter such that the lumen through the hub portion is in fluid communication with the catheter lumen.

The lumen extending through the hub includes a wall having an average wall thickness. The strain relief passage also has a wall having an average wall thickness. In a preferred embodiment, the average wall thickness of the hub portion is greater than the average wall thickness of the strain relief passage. In one embodiment, the wall thickness of the passage generally decreases from the strain relief proximal end toward the strain relief distal end.

In a preferred embodiment, a plurality of grooves extend into the passage wall generally transversely toward the passage. The grooves can extend through the wall into the passage. The grooves can be disposed in a plurality of sets, each set including two grooves. The two grooves within each set can be disposed generally within the same plane to define a point of flexibility or transverse hinge in the strain relief. In an alternate embodiment, the strain relief can include a generally helical portion. The helical portion preferably extends from proximate the proximal end of the strain relief to proximate the distal end of the strain relief.

In an alternate embodiment, the hub portion may include an angled port. The angled port, hub portion and strain relief portion can be integrally formed or connected by insert molding to form a manifold for an angioplasty catheter. The angled port defines a lumen in fluid communication with the lumen defined through the hub portion, and consequently the port is also in fluid communication with the lumen of the catheter tube held within the strain relief portion. If the angioplasty catheter is an over-the-wire catheter, a separate guide wire tube defining a guide wire lumen can extend through the catheter tube defining an inflation lumen between the catheter tube and the guide wire tube therein. The tube defining the guide wire lumen can include a separate hub portion connectable to the proximal end of the hub portion of the manifold.

The connector can be a threaded connector. The hub portion can include transversely extending wings. The hub portion, the strain relief portion and angled port can be made from the same material, such as nylon, PEBA (polyether block amide polymer, commercially available under the trade name PEBAX), polycarbonate or another material having similar properties.

BRIEF DESCRIPTION OF THE DRAWINGS

FIG. 6 discloses a perspective view of the manifold of FIG. 4 and the hub and guide wire tube of FIG. 5 inserted therein.

DETAILED DESCRIPTION OF THE INVENTION

Figure 1:
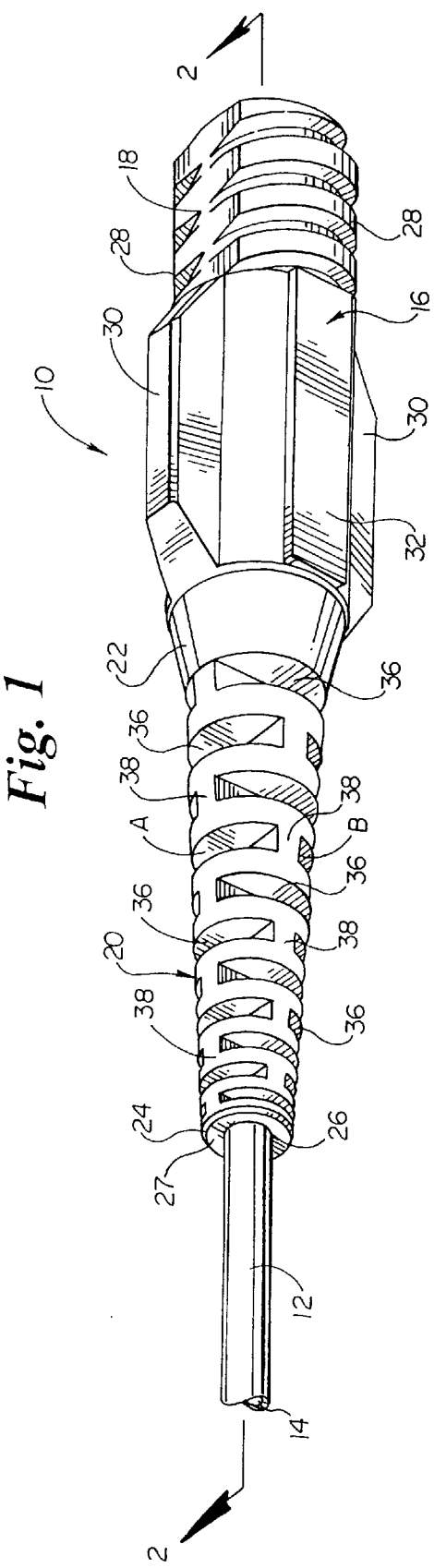
FIG. 1 discloses a perspective view of a hub assembly in accordance with the present invention.

Referring now to the drawings wherein like reference numerals refer to the same elements throughout the several views, a hub assembly in accordance with the present invention is referred to generally by reference numeral 10 in FIG. 1. Hub assembly 10 is preferably connectable to an end of a catheter tube 12 which has a lumen 14 extending therethrough. Catheter hub assembly 10 has an axial length defined along the section line 2—2 shown in FIG. 1. The proximal end of hub portion 16 includes an integral connector 18. A strain relief 20 having a proximal end 22 and distal end 24 is integrally connected at proximal end 22 to the distal end of hub portion 16. Strain relief 20 preferably has a flexibility between that of hub portion 16 and catheter tube 12. Strain relief 20 includes a passage 26 which has a lumen wall 27. Passage 26 extends from distal end 24 to proximal end 22. Passage 26 is configured to receive an end of catheter tube 12.

Integral connector 18 of hub portion 16 preferably includes threads 28 for threadable connection to a Y-adaptor, inflation device or other devices as well known in the medical arts. Rather than threads 28, connector 18 could include a transversely extending flange, bayonets, or other connector means.

Hub portion 16 preferably includes transversely extending wings 30. Hub portion 16 can also include additional texturing provided by a raised portion such as rectangular print pad 32. An operator can push against the sides of wing 30 to rotate hub assembly 10 to, for example, thread integral connector 18 into a Y-adaptor or other device or rotate catheter tube 12 for some therapeutic or diagnostic purpose. Similarly, the texturing or hub portion 16 provides a rough surface to assist an operator to grip hub assembly 10.

Figure 2:
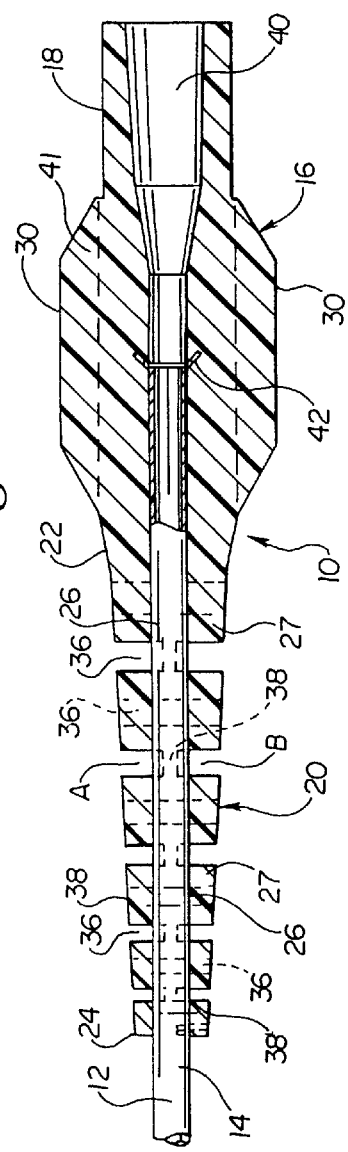
FIG. 2 discloses a cross-section of the hub assembly of FIG. 1.

Referring now to FIGS. 1 and 2, strain relief 20 can include grooves 36 extending transversely into strain relief 20 toward passage 26. The width and spacing of grooves 36 may be varied to effect the flexibility of strain relief 20. Grooves 36 may be arranged in transversely oppositely disposed sets of two, for example, grooves A and B. Each groove within a set can extend through strain relief 20 to passage 26 leaving a thin portion 38 of strain relief 20 disposed between the oppositely disposed grooves 36. Grooves 36 need not extend through to passage 26, but not extending grooves 36 through to passage 26 will reduce the flexibility of strain relief 20. Strain relief 20 is preferably more flexible at distal end 24 than at proximal end 22.

Thin portion 38 provides a point of flexibility or transverse hinge in strain relief 20. For example, as a generally transverse bending force is applied to strain relief 20, grooves on the opposite side of strain relief 20 from the bending force will tend to close as grooves on the same side of the strain relief as the force tend to open. Because a bending force may be applied to any side of strain relief 20, it is preferable to vary the orientation of grooves 36 and thin portions 38 around strain relief 20. For example, as shown in FIGS. 1 and 2, each successive set of grooves 36 is rotated 90° from the preceding set.

Referring now to FIG. 2, a lumen 40 having a luminal wall 41 is shown extending from the proximal end to the distal end of hub portion 16. Lumen 40 is in fluid communication with catheter lumen 14. The extreme end of catheter tube 12 includes a transversely flared portion 42 embedded in wall 41 of lumen 40. In a preferred embodiment of hub assembly 10, to provide greater flexibility of strain relief 20 relative to hub portion 16, the average thickness of wall 41 is greater than the average thickness of strain relief wall 27. The thickness of wall 27 may also taper between proximal end 22 and distal end 24 of strain relief 20.

Figure 3:
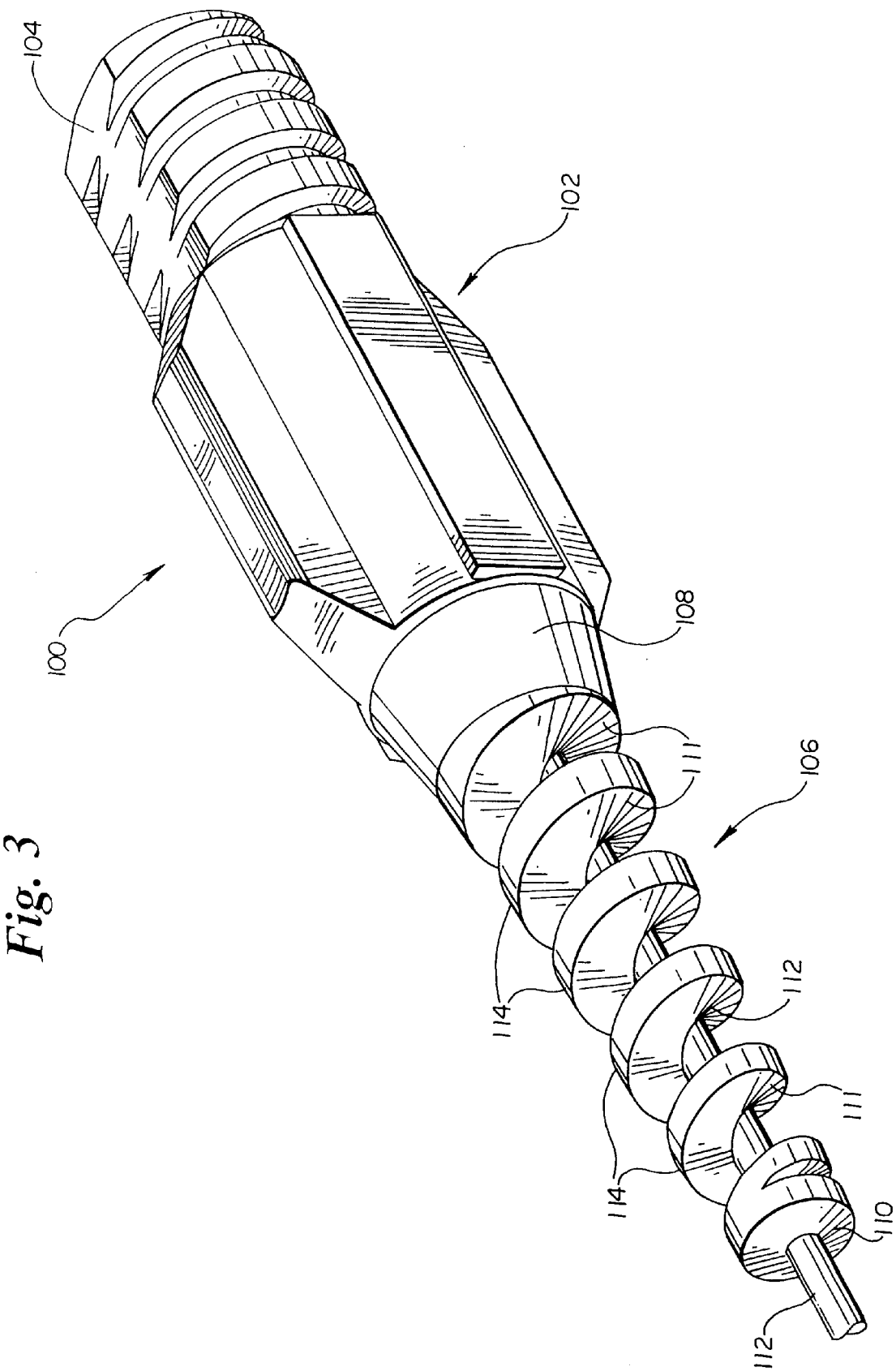
FIG. 3 discloses a perspective view of an alternate embodiment of a hub assembly in accordance with the present invention.
Figure 4:
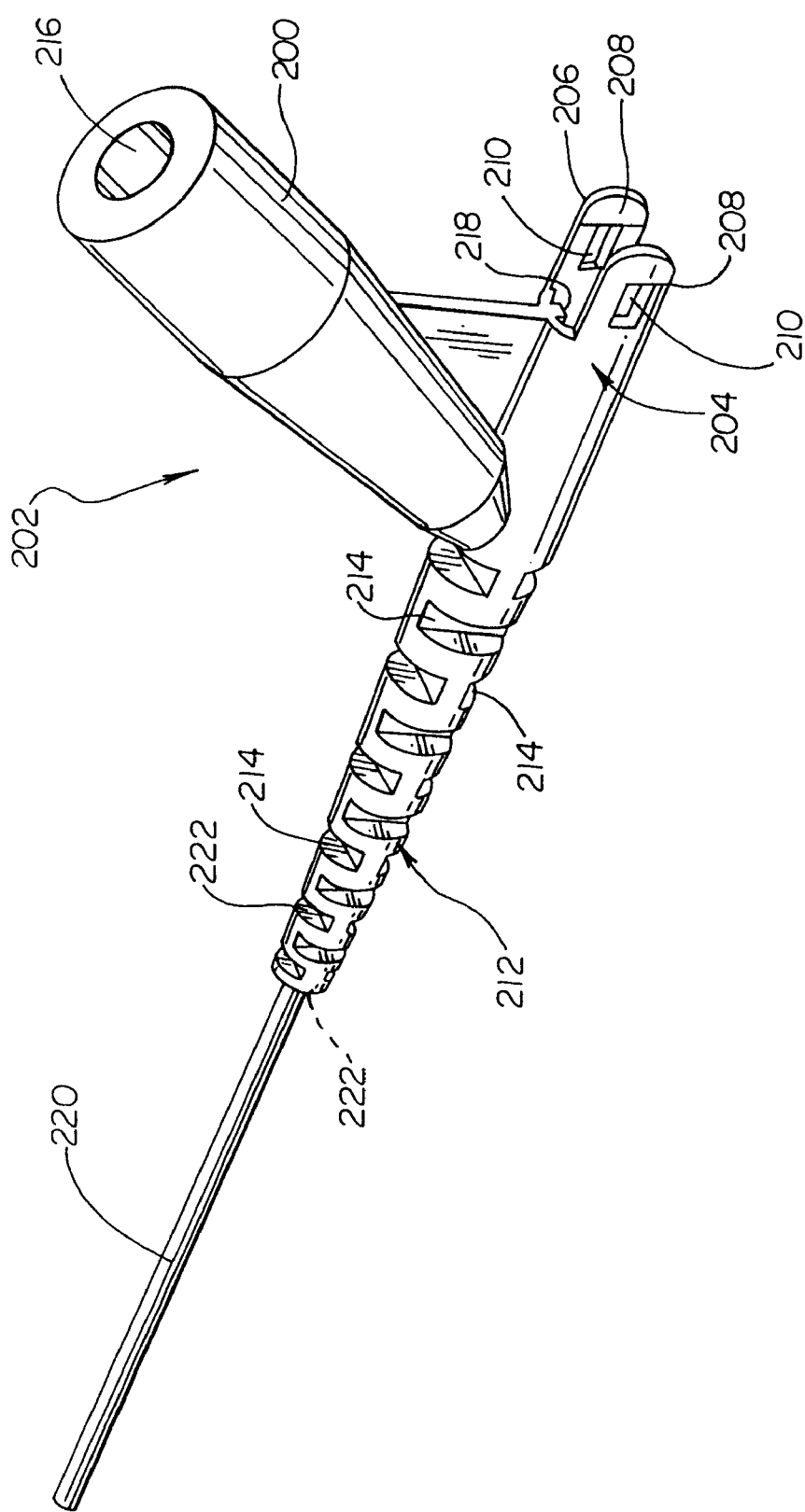
FIG. 4 discloses a perspective view of an alternative embodiment of the hub assembly in accordance with the present invention including an angled port forming a manifold.

FIG. 3 is a perspective view of an alternative embodiment of a hub assembly 100 in accordance with the present invention. Hub assembly 100 includes a hub portion 102 having an integral connector 104. Hub assembly 100 includes a strain relief 106 which has a proximal end 108 and a distal end 110 and a wall 111. Strain relief 106 is formed in a helical shape defining a passage 112 which is configured to receive an end of a catheter tube. The helix of strain relief 106 includes a series of bends 114. Each bend 114 is preferably spaced from the adjacent bend 114. The space between the bends provides a point of flexibility or hinge in strain relief 106. Other than the strain relief 106, hub assembly 100 can in all respects be similar to hub assembly 10. The average thickness of strain relief wall 111 can be less than the average wall thickness of the lumen through hub portion 102.

The hub assembly of the present invention may be modified by including an angled port 200 to form a manifold 202. Manifold 202 includes a hub portion 204 having a proximal end and a distal end and an integral connector 206 at the proximal end. Connector 206 can include two oppositely disposed tabs 208, each including an opening 210 therethrough. Integrally connected to the distal end of hub portion 204 is a strain relief 212. The strain relief 212 includes an arrangement of grooves 214 substantially similar to the arrangement of grooves 36 of strain relief 20.

Angled port 200 defines a lumen 216 extending therethrough to a lumen 218 extending through hub 204. An end of a catheter tube 220 extends through a passage 222 defined by strain relief 212 into lumen 218 of hub portion 204. The extreme end of tube 220 can be anchored in hub portion 204 in the same manner as transversely flared portion 42 of hub assembly 10 described above. The end of tube 220 is anchored within hub 204 distally of the opening of lumen 216 of angle port 200 such that the lumen defined by tube 220 is in fluid communication with port lumen 216 and lumen 218 of hub portion 204.

Figure 5:
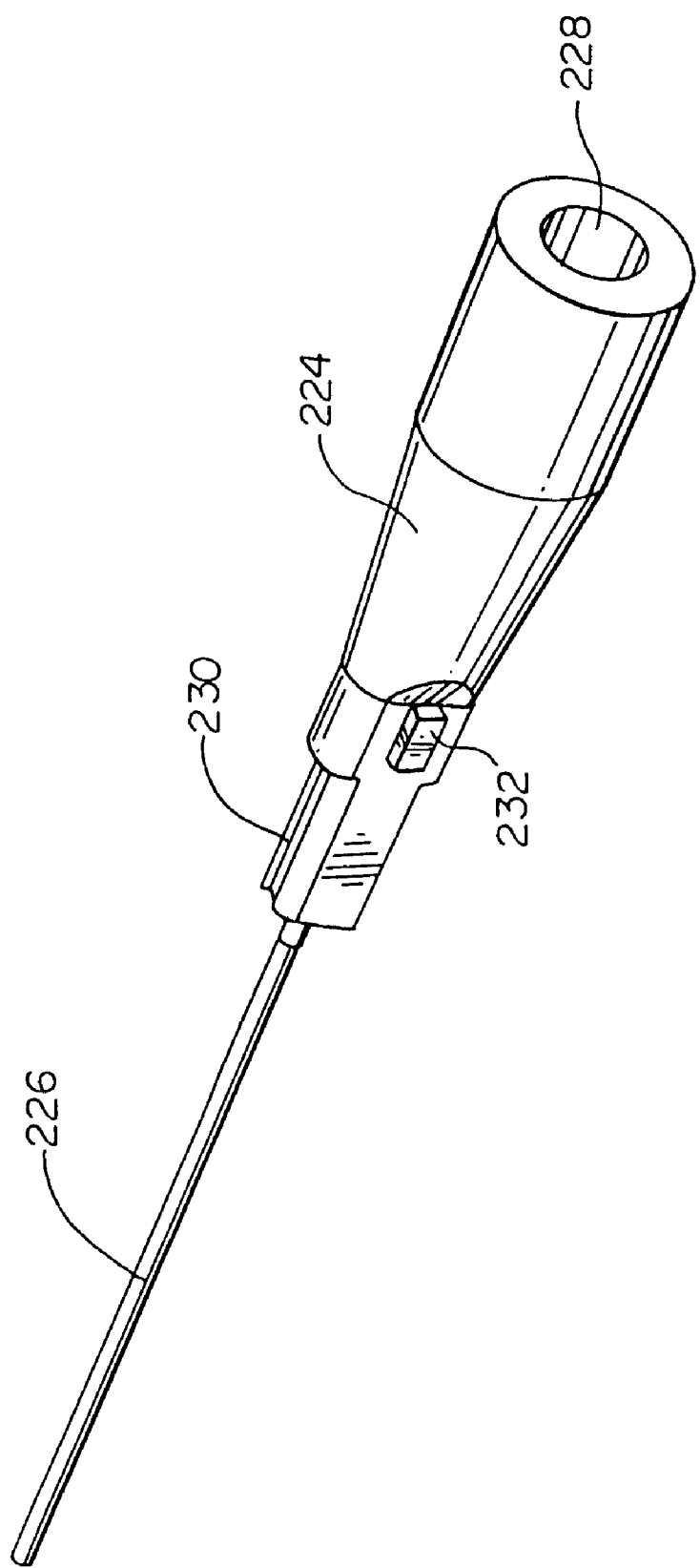
FIG. 5 discloses a perspective view of a hub for a guide wire tube insertable into the manifold of FIG. 4.

FIG. 5 shows a hub 224 affixed to an end of a guide wire tube 226. Hub 224 includes a longitudinally extending lumen 228 in fluid communication with a guide wire lumen through guide wire tube 226. The end of tube 226 within hub 224 may be anchored like flared end 42 of hub assembly 10 described above. Hub 224 includes an insertable portion 230 and two oppositely disposed bayonets 232 (one of which is hidden from view in FIG. 5).

As shown in FIG. 6, guide wire tube 226 has been inserted into catheter tube 220 through hub portion 204 of manifold 202. Insertable portion 230 is inserted into lumen 218 of hub portion 204 such that bayonets 232 are inserted through holes 210 of tabs 208 to connect hub 224 to manifold 202. As known to those skilled in the art, in such a configuration, a guide wire can extend through the guide wire lumen, hub portion lumen 218 and hub lumen 228 for normal use. An inflation lumen in fluid communication with port lumen 216 is defined within catheter tube 220 between guide wire tube 226 and tube 220.

The hub and manifold assemblies of the present invention are preferably integrally molded in one piece. The hub assembly is preferably formed by insert molding. In this process, a mandrel is inserted into the end of a catheter tube. A portion of the mandrel preferably extends from the end of the catheter tube. The catheter tube and mandrel are placed within the mold. Molten material is injected into the mold around the end of the catheter and the mandrel to form the integral hub assembly on the end of the catheter tube. Other standard molding techniques as well known in the art may be used to integrally mold the hub assembly of the present invention.

Material such as PEBA (polyether block amide polymer, commercially available under the trade name PEBAX), ISOPLAST (engineering thermoplastic polyurethane) or other polyurethanes, nylon, polycarbonate, ULTEM, polyetherimide polyester polycaprolactone, and high density polyethylene or similar material may be used to form the hub and manifold assemblies of the present invention. Depending upon the specific use of the hub assembly, the flexural modulus of the material to be used is preferably between 60,000 and 500,000 psi. However, materials having a higher or lower flexural modulus can be used depending upon the particular application for the hub assembly. For example, materials having a higher flexural modulus can be used with a relatively stiff catheter tube whereas materials having a lower flexural modulus can be used with relatively more flexible catheter tubes.

Numerous characteristics and advantages of the invention covered by this document have been set forth in the foregoing description. It will be understood, however, that this disclosure is, in many respects, only illustrative. Changes may be made in details, particularly in matters of shape, size, and arrangement of parts without exceeding the scope of the invention. The invention's scope is, of course, defined in the language in which the appended claims are expressed.

What is claimed is:

1. A method of manufacturing a hub assembly for a catheter tube having a lumen therethrough, comprising the step of:

molding monolithically the hub assembly including a hub portion having a first rigidity, and a strain relief portion having a second rigidity less than the first rigidity to the catheter tube;

the hub portion having a proximal end, a distal end, a wall, a connection disposed at the proximal end, and a lumen defined therethrough extending from the proximal end to the distal end;

the strain relief having a proximal end, a distal end, and a wall, the strain relief being disposed at the distal end of the hub portion and the proximal end of the strain relief forming a continuous piece with the distal end of the hub portion, the strain relief defining a passage receiving the catheter tube such that the lumen through the hub portion is in fluid communication with the catheter lumen; and at least one groove extending into the strain relief wall, wherein the at least one groove extends through the wall into the passage.

2. The method in accordance with claim 1, wherein the at least one groove extends into the strain relief wall generally transversely toward the passage.

3. The method in accordance with claim 2, the hub assembly further comprising a plurality of grooves disposed in a plurality of sets, each set including two grooves, the two grooves within each set being disposed generally within the same plane to define a transverse hinge in the strain relief.

4. The method in accordance with claim 1, wherein the connector is a threaded connector.

5. The method in accordance with claim 1, wherein the hub portion further includes transversely extending wings.

6. The method in accordance with claim 1, wherein the hub portion and the strain relief portion comprise the same material.

7. The method in accordance with claim 6, wherein the material comprises nylon.

8. The method in accordance with claim 6, wherein the material comprises PEBA.

9. The method in accordance with claim 6, wherein the material comprises polycarbonate.

10. The method in accordance with claim 1, wherein the hub assembly further comprises an angled port integrally connected to, and extending from, the hub portion.

11. The method in accordance with claim 1, wherein the strain relief wall thickness generally decreases from the strain relief proximal end to the strain relief distal end.

12. The method in accordance with claim 1, wherein the wall of the hub portion has an average wall thickness and the wall of the strain relief has an average wall thickness;

wherein the average wall thickness of the hub portion wall is greater than the average wall thickness of the strain relief wall.

13. A method of manufacturing a hub assembly for a catheter tube having a lumen therethrough, comprising the step of:

molding monolithically the hub assembly including a hub portion having a first rigidity, and a strain relief portion having a second rigidity less than the first rigidity to the catheter tube;

the hub portion having a proximal end, a distal end, a wall, a connection disposed at the proximal end, and a lumen defined therethrough extending from the proximal end to the distal end;

the strain relief having a proximal end, a distal end, and a wall, the strain relief being disposed at the distal end of the hub portion and the proximal end of the strain relief forming a continuous piece with the distal end of the hub portion, the strain relief defining a passage receiving the catheter tube such that the lumen through the hub portion is in fluid communication with the catheter lumen, wherein the hub portion and the strain relief portion comprise the same material; and at least one groove extending into the strain relief wall.

14. The method in accordance with claim 13, wherein the at least one groove extends into the strain relief wall generally transversely toward the passage.

15. The method in accordance with claim 14, wherein the at least one groove extends through the wall into the passage.

16. The method in accordance with claim 14, the hub assembly further comprising a plurality of grooves disposed in a plurality of sets, each set including two grooves, the two grooves within each set being disposed generally within the same plane to define a transverse hinge in the strain relief.

17. The method in accordance with claim 13, wherein the connector is a threaded connector.

18. The method in accordance with claim 13, wherein the hub portion further includes transversely extending wings.

19. The method in accordance with claim 13, wherein the material comprises nylon.

20. The method in accordance with claim 13, wherein the material comprises PEBA.

21. The method in accordance with claim 13, wherein the material comprises polycarbonate.

22. The method in accordance with claim 13, wherein the hub assembly further comprises an angled port integrally connected to, and extending from, the hub portion.

23. The method in accordance with claim 13, wherein the strain relief wall thickness generally decreases from the strain relief proximal end to the strain relief distal end.

24. The method in accordance with claim 13, wherein the wall of the hub portion has an average wall thickness and the wall of the strain relief has an average wall thickness;
   wherein the average wall thickness of the hub portion wall is greater than the average wall thickness of the strain relief wall.

\* \* \* \* \*